(12) United States Patent
Tweedie et al.

(10) Patent No.: US 11,660,409 B2
(45) Date of Patent: May 30, 2023

(54) ELECTRONIC MODULE FOR AN INHALER AND INHALER ASSEMBLY COMPRISING THE ELECTRONIC MODULE

(71) Applicant: CHIESI FARMACEUTICI S.P.A., Parma (IT)

(72) Inventors: Alan Tweedie, Parma (IT); Colin Mitchell, Parma (IT); Scott Lewis, Parma (IT); Andrew T. Heidt, Parma (IT); Robert Rudolf, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 0 days.

(21) Appl. No.: 17/780,503

(22) PCT Filed: Nov. 27, 2020

(86) PCT No.: PCT/EP2020/083759
§ 371 (c)(1),
(2) Date: May 26, 2022

(87) PCT Pub. No.: WO2021/105445
PCT Pub. Date: Jun. 3, 2021

(65) Prior Publication Data
US 2023/0001111 A1 Jan. 5, 2023

(30) Foreign Application Priority Data
Nov. 28, 2019 (EP) .................... 19212224

(51) Int. Cl.
*A61M 15/00* (2006.01)
(52) U.S. Cl.
CPC ...... *A61M 15/008* (2014.02); *A61M 15/0026* (2014.02); *A61M 15/0096* (2014.02);
(Continued)

(58) Field of Classification Search
CPC .................... A61M 15/008; A61M 2205/8206
See application file for complete search history.

(56) References Cited

U.S. PATENT DOCUMENTS

| 5,505,195 A | 4/1996 | Wolf et al. |
| 5,657,748 A | 8/1997 | Braithwaite |
| (Continued) | | |

FOREIGN PATENT DOCUMENTS

| EP | 2119465 A1 | 11/2009 |
| EP | 2414978 A1 | 2/2012 |
| (Continued) | | |

OTHER PUBLICATIONS

International Search Report and Written Opinion for International Application No. PCT/EP2020/083751 filed on Nov. 27, 2020 on behalf of Chiesti Farmaceutici S.P.A. dated Dec. 22, 2020, 17 pages.
(Continued)

*Primary Examiner* — Kathryn E Ditmer
(74) *Attorney, Agent, or Firm* — Steinfl + Bruno, LLP

(57) ABSTRACT

An electronic module for an inhaler includes a printed circuit board and electronic components configured to detect at least a status and/or at least a working parameter of the inhaler when the electronic module is attached to the inhaler. A battery is permanently joined to the printed circuit board. A first terminal and a second terminal are electrically connectable one to the other through a main switch to close a circuit between the battery and the electronic components. In a rest configuration, the first and second terminals are electrically separated by the main switch. In a work configuration, the first terminal and the second terminal are electrically connected one to the other through the main switch.

20 Claims, 7 Drawing Sheets

(52) U.S. Cl.
CPC ............... *A61M 2202/064* (2013.01); *A61M 2205/8206* (2013.01)

(56) References Cited

U.S. PATENT DOCUMENTS

| | | | |
|---|---|---|---|
| 5,809,997 A * | 9/1998 | Wolf | A61M 15/0005 |
| | | | 128/200.23 |
| 6,182,655 B1 | 2/2001 | Keller et al. | |
| 6,377,848 B1 | 4/2002 | Garde et al. | |
| 2005/0028815 A1 | 2/2005 | Deaton et al. | |
| 2005/0251289 A1 | 11/2005 | Bonney et al. | |
| 2009/0114219 A1 | 5/2009 | Ferris et al. | |
| 2014/0158126 A1 | 6/2014 | Parry-Billings et al. | |
| 2018/0070634 A1 * | 3/2018 | Sur | A61M 15/06 |
| 2018/0140788 A1 * | 5/2018 | Calderon Oliveras | A61B 5/4833 |
| 2018/0348075 A1 | 12/2018 | Rubinstein et al. | |
| 2019/0117919 A1 * | 4/2019 | Panarello | A61M 16/0003 |
| 2022/0218920 A1 * | 7/2022 | Roche | A61M 15/0001 |
| 2023/0016850 A1 | 1/2023 | Tweedie et al. | |

FOREIGN PATENT DOCUMENTS

| | | | |
|---|---|---|---|
| EP | 3113817 A1 | 1/2017 | |
| EP | 3501584 A1 | 6/2019 | |
| WO | 03/092576 A2 | 11/2003 | |
| WO | 2004/012801 A1 | 2/2004 | |
| WO | 2010/114392 A1 | 10/2010 | |
| WO | WO-2014150247 A1 * | 9/2014 | ............. A24F 40/50 |
| WO | 2015/133909 A1 | 9/2015 | |
| WO | 2016/000983 A1 | 1/2016 | |
| WO | 2017/178865 A1 | 10/2017 | |
| WO | 2019/021254 A1 | 1/2019 | |
| WO | 2021/105440 A1 | 6/2021 | |

OTHER PUBLICATIONS

International Search Report and Written Opinion for International Application No. PCT/EP2020/083759 filed on Nov. 27, 2020 on behalf of Chiesti Farmaceutici S.P.A. dated Jan. 20, 2021, 14 pages.

* cited by examiner

ELECTRONIC MODULE FOR AN INHALER AND INHALER ASSEMBLY COMPRISING THE ELECTRONIC MODULE

CROSS-REFERENCE TO RELATED APPLICATIONS

The present application is the U.S. National Stage of International Patent Application No. PCT/EP2020/083759 filed on Nov. 27, 2020 which, in turn, claims priority to European Patent Application No. 19212224.0 filed on Nov. 28, 2019.

TECHNICAL FIELD OF THE INVENTION

The present invention relates an electronic module for an inhaler and to an assembly comprising an inhaler and the electronic module. The inhaler is preferably a device for dispensing a powdered medicament preparation by inhalation. The device is in particular a portable, multiple-dose, breath activated dry powder inhaler without propellant gas, equipped with a metering device which dispenses doses from a medicament container. The electronic module is configured to detect at least a status and/or at least a working parameter of the inhaler and, possibly, to perform other related functions.

Background Art

The administering of a powdered medicament preparation by inhalation from an inhaler is commonly known. Multiple-dose type powder inhalers comprising a powder container and a metering member which measures and dispenses a unit dose are also known.

Document WO 2004/012801, of the same Applicant, discloses a powder inhaler comprising a container for storing a powdered medicament, a metering member having a dosing recess to be filled with a dose of the powdered medicament and a mouthpiece in communication with an inhalation channel of the powder inhaler. The powder inhaler comprises a protective member which is slidingly moveable on the metering member between a closed position, in which the protective member covers the dosing recess of the metering member if the metering member is in an inhalation position, and an open position, in which the protective member exposes the dosing recess thereby enabling inhalation of the dose of the powdered medicament contained in the dosing recess. The protective member is coupled to an inhalation actuated mechanism in such a manner that the inhalation actuated mechanism moves the protective member from its closed position to its open position if there is an inhalation suction force exerted by a user which exceeds a predetermined level. The mechanical structure of the powder inhaler of WO 2004/012801 is able to provide a powder inhaler with an improved dosing ability, whereby unintended dosing can be avoided. Nowadays every user owns an electronic device, such as a computer, a smartphone or a tablet, with applications which could be used in everyday life and which could be useful to manage administering of medicaments. Document WO 2016/000983A1, by the same Applicant, discloses a powder inhaler similar to the one of WO 2004/012801.

The powder inhaler of WO 2004/012801 and of WO2016000983A1 do not comprise any electronic device to interface with an external electronic device.

Inhalers provided with electronic devices configured to detect actuation of the inhaler itself and/or to collect data are also known.

Document EP2414978 discloses a reusable and portable communications device which may be fitted to an electronic medicament delivery device, such as electronic medicament inhalers. The communications device may include a battery for powering the device. The battery may be a disposable battery or a rechargeable battery.

Document EP3113817 discloses a compliance monitor for a dry powder medicament delivery device. The compliance monitor includes a first portion for receiving and/or retaining a base portion of the medicament delivery device and a second portion for releasably securing the medicament delivery device to the first portion. The compliance monitor may be powered by a battery (rechargeable or replaceable), a kinetic charger, or by solar power.

Document WO2017178865 discloses an add-on device for a metered dose inhaler. The add-on device comprises an observance system housing component comprising an observance system with at least one pressure sensor. The observance system allows to register certain predefined events. The device comprises a power supply, for example a removable and/or rechargeable battery. The use of rechargeable batteries cited in some documents above implies the adoption of a battery charger, which may raise the costs of the device.

The use of replaceable batteries cited in some other documents above implies that the connection between the batteries and the device, such as contacts of a printed circuit board, do not provide a power supply that is robust to mechanical forces, such as those occurring during dropping of the device or various shocks and vibrations. Indeed, commonly used battery holders that allow removing and re-insertion of the battery cells are liable to deform during shocks and mechanical disturbances, hence causing interruptions in the supply of electrical power from the battery to the electronic circuitry (as the battery temporarily loses contact with the battery holder and/or the printed circuit board). These power interruptions cause the resetting of electronic control units of known devices, which may cause permanent software failure depending on the internal state of the control unit at the point when its power supply was lost.

Document U.S. Pat. No. 5,505,195 discloses a dry powder inhalant device adapted for mounting on a conventional medication dry powder dispenser having a mouthpiece incorporated in one end of the dispenser. The device is designed for monitoring prescribed dosages of dry powder medication received through the mouthpiece, the lips and into the mouth, throat, and respiratory system of a user of the device. The device includes main batteries which are the main power to the device and a further battery to power a ram memory if main batteries are ever removed or become low in energy. The redundant power supply of U.S. Pat. No. 5,505,195 is not cost effective.

SUMMARY

It is an object of the present invention to eliminate the above drawbacks of hitherto known electronic modules for inhalers.

In particular, it is an object of the present invention to provide an electronic module for inhalers with a power supply that is robust to mechanical forces, thus preventing power failures.

It is also object of the present invention to provide an electronic module for inhalers which allows to preserve the battery at least between the production of the device and its first use, i.e. during a long-term storage before the sale of the same.

It is a further object of the present invention to minimize the power load presented to the battery during the long-term storage.

At least one of the above objects is substantially achieved by an electronic module for an inhaler and to an inhaler assembly according to one or more of the appended claims and/or of the following aspects.

Aspects of the invention are disclosed in the following.

In accordance with a $1^{st}$ independent aspect, an electronic module for an inhaler, wherein the electronic module is attached or attachable to the inhaler, comprises: a printed circuit board comprising electronic components, wherein the electronic components are configured to detect at least a status and/or at least a working parameter of the inhaler when the electronic module is attached to the inhaler;

at least one battery permanently joined to the printed circuit board;

wherein the printed circuit board comprises a first terminal and a second terminal electrically connectable one to the other through a main switch to close a circuit between the battery and the electronic components to power on the electronic components;

wherein, in a rest configuration of the electronic module, the first terminal and the second terminal are electrically separated by the main switch;

wherein, in a work configuration of the electronic module, the first terminal and the second terminal are electrically connected one to the other through said main switch;

a latching circuit operatively electrically interposed between the battery and the electronic components, wherein, when the electronic module is in the work configuration, the latching circuit is configured to maintain power supply to the electronic components during momentary disconnections of the first terminal from the second terminal due to a fault of the main switch.

In an aspect according to the first aspect, the electronic module optionally comprises a removable electrical insulating pull-tab; wherein the main switch comprises at least one spring loaded contact; wherein, in the rest configuration of the electronic module, the first terminal and the second terminal are electrically separated by the removable electrical insulating pull-tab; wherein, in the work configuration of the electronic module, the removable electrical insulating pull-tab is removed and the first terminal and the second terminal are electrically connected one to the other through said at least one spring loaded contact; the latching circuit being configured to maintain power supply to the electronic components during momentary disconnections of the first terminal from the second terminal due to shocks and/or vibrations causing the temporary loss of the spring loaded contact.

In accordance with a $2^{nd}$ independent aspect, an electronic module for an inhaler, wherein the electronic module is attached or attachable to the inhaler, comprises: a printed circuit board comprising electronic components, wherein the electronic components are configured to detect at least a status and/or at least a working parameter of the inhaler when the electronic module is attached to the inhaler;

at least one battery permanently joined to the printed circuit board;

wherein the printed circuit board comprises a first terminal and a second terminal electrically connectable one to the other through at least one spring loaded contact to close a circuit between the battery and the electronic components to power on the electronic components;

a removable electrical insulating pull-tab;

wherein, in a rest configuration of the electronic module, the first terminal and the second terminal are electrically separated by the removable electrical insulating pull-tab;

wherein, in a work configuration of the electronic module, the removable electrical insulating pull-tab is removed and the first terminal and the second terminal are electrically connected one to the other through said at least one spring loaded contact.

In an aspect according to the second aspect, the electronic module optionally comprises a latching circuit operatively electrically interposed between the battery and the electronic components, wherein, when the electronic module is in the work configuration, the latching circuit is configured to maintain power on of the electronic components during momentary disconnections of the first terminal from the second terminal due to shocks and/or vibrations causing the temporary loss of the spring loaded contact.

In a $3^{rd}$ independent aspect, an inhaler assembly comprises:

an inhaler;

the electronic module according to any of the preceding aspects or according to one or more of the following aspects;

wherein the electronic module is attached or is configured to be attached in removable manner to the inhaler; wherein the electronic module is configured to detect at least a status and/or at least a working parameter of the inhaler when the electronic module is attached to the inhaler.

The Applicant verified that the invention allows, when the electronic module is operative, to prevent power failures of the electronic module due to a fault of the main switch (e.g. of said at least one spring loaded contact) and following interruptions of electrical contacts between the battery (or batteries) and the printed circuit board. Indeed, since the battery is permanently joined to the printed circuit board, momentary faults of the main switch due for example to shocks and/or vibrations cannot cause contact losses. In the present description and in the attached claims, the term "permanently connected" means that the battery cannot be removed from the printed circuit board without breaking the physical contacts.

In particular, the Applicant verified that, in the event that, during mechanical shocks and vibrations, the at least one sprung loaded contact is temporarily lost, the latching circuit is able to avoid disconnection of power supply from the battery to the electronic components of the electronic module.

Using this latching load-switch circuit design provides a solution that minimizes the power consumption of the electronic module during its storage life whilst ensuring that the power supplied from the batteries is robust against mechanical shocks and vibrations. The Applicant verified that the invention allows to preserve the battery and to minimize the power load presented to the battery during the long-term storage. Indeed, the removable electrical insulating pull-tab, inserted into the electronic module during manufacturing and removed by the user before the first use, prevents connection between the battery and electronic circuits of the printed circuit board and preserve battery life during long-term storage.

In an aspect, the electronic module is removably attachable to the powder inhaler, optionally through a clip-on coupling. Coupling and uncoupling is easy and fast.

In an aspect, the electronic module, once detached from a powder inhaler, is re-usable with another powder inhaler.

The same electronic module may be used with another new powder inhaler once the medicament in an old inhaler is over.

The electronic module is intended to be supplied separately from the inhaler and to be assembled by the user upon first-time use.

In an aspect, the removable electrical insulating pull-tab, once removed, cannot be inserted again to separate the first terminal from the second terminal.

In an aspect, the removable electrical insulating pull-tab is disposable.

In an aspect, the latching circuit comprises a load switch.

In an aspect, the load switch has an input, an output and an enable input.

In an aspect, the first terminal is electrically connected to the battery and to the input.

In an aspect, the second terminal is electrically connected to the enable input.

In an aspect, the electronic components are electrically connected to the output.

In an aspect, the load switch comprises a feedback electrical path electrically connecting the output of the load switch to the enable input of the load switch.

In an aspect, the feedback electrical path comprises a passive component or an active component.

In an aspect, the passive component is a feedback resistor.

In an aspect, the feedback resistor is higher than 50 kOhm.

In an aspect, the feedback resistor is lower than 150 kOhm.

In an aspect, the feedback resistor is higher than 80 kOhm.

In an aspect, the feedback resistor is lower than 120 kOhm.

In an aspect, the passive components is a diode.

In an aspect, the active component is a microcontroller or a processing circuitry.

In an aspect, when the electronic module is in the rest configuration, the latching circuit provides isolation of the battery from the electronic components.

In an aspect, when the main switch is on or the removable electrical insulating pull-tab is removed and the first terminal and the second terminal are electrically connected one to the other, the load switch is enabled and electrically connects the input to the output to power the electronic components.

In an aspect, during momentary disconnections of the first terminal from the second terminal due to a fault of the main switch or of said spring loaded contact, e.g. due to shocks and/or vibrations, a signal in the feedback electrical path is configured to keep the load switch enabled and to keep the electronic components powered on.

In an aspect, the load switch has a quiescent current comparable to a self-discharge rate of said at least one battery.

In an aspect, the quiescent current is less than 2 µA, optionally less than 1 µA.

Applicant verified that the load switch adds minimal additional energy demand to the system.

In an aspect, the at least one battery is soldered to the printed circuit board, optionally using through-hole mounted tabs.

In an aspect, the at least one battery comprises a plurality of batteries, optionally a battery pack.

In an aspect, the batteries are permanently joined together, optionally welded together, optionally using metallic tabs.

Soldering and/or welding ensure a safe and robust electric contact.

In an aspect, the at least one battery is non-rechargeable.

The electronic module is disposable, once the at least one battery is discharged, it is not reusable.

In an aspect, the removable electrical insulating pull-tab is made of plastic.

In an aspect, the removable electrical insulating pull-tab is a film.

In an aspect, the removable electrical insulating pull-tab comprises an isolating part electrically separating or configured to electrically separate the first terminal from the second terminal.

In an aspect, the removable electrical insulating pull-tab comprises a portion configured to be grabbed by hand to allow removing said removable electrical insulating pull-tab.

In an aspect, the electronic module comprises a housing.

In an aspect, the printed circuit board is placed inside the housing.

In an aspect, the removable electrical insulating pull-tab has a portion protruding from the housing to allow manually removing said removable electrical insulating pull-tab.

In an aspect, the removable electrical insulating pull-tab has an easy thumb-grip area to facilitate removal.

In an aspect, said at least one spring loaded contact comprises a metal spring.

In an aspect, in the rest configuration of the electronic module, the removable electrical insulating pull-tab is interposed between the metal spring and the first terminal and second terminal.

In an aspect, in the work configuration of the electronic module, the metal spring is elastically held against the first terminal and the second terminal and electrically connects the first terminal to the second terminal and may momentarily disconnect from the first terminal and/or from the second terminal due to said shocks and/or vibrations.

In an aspect, the first terminal and second terminal are pads, optionally copper pads, on the printed circuit board.

In an aspect, the metal spring is a metal leaf having a first end joined to the printed circuit board or to a housing of the electronic module and a second end elastically held against the first terminal and the second terminal.

In an aspect, the main switch is a magnetic switch or an optical switch or a relay or an opto-coupler or a touch switch.

In an aspect, the electronic components comprise: an electronic control unit, optionally a microprocessor, and at least one sensor operatively connected to the electronic control unit and configured to detect said at least a status and/or said at least a working parameter of the inhaler.

In an aspect, the electronic components comprise a storage memory.

In an aspect, the electronic components comprise a communication interface, optionally a wireless communication interface, optionally a Bluetooth communication interface.

In an aspect, the communication interface is configured to connect the electronic module to an external electronic device, such as a computer, a smartphone, a tablet or the like. All the working parameters and data of the inhaler detected through the electronic module may be transferred to the external electronic device.

In an aspect, the electronic module comprises a button switch operatively connected to the wireless communication interface to start pairing the electronic module to the external electronic device.

In an aspect, the button switch is the main switch or is operatively connected to the main switch such that transition of the electronic module from the rest configuration to the working configuration is triggered through the button switch.

In an aspect, the inhaler is a powder inhaler.

In an aspect, the inhaler comprises a container for storing a powdered medicament.

In an aspect, the container is filled or is configured to be filled with an amount of powder medicament corresponding to a plurality of doses, optionally to 100-200 doses.

In an aspect, the inhaler comprises a mouthpiece and an inhalation channel connected to the mouthpiece.

In an aspect, the inhaler comprises: a metering device having a dosing recess.

In an aspect, the metering device is movable, with respect to the container and the inhalation channel, between an idle state, in which the dosing recess is in communication with an opening of the container so as to be filled with a dose of the powdered medicament, and a triggered state, in which the dosing recess is in communication with the inhalation channel for enabling inhalation of the dose of the powdered medicament contained in the dosing recess through the mouthpiece.

In an aspect, the electronic components of the electronic module comprise: a sensor positioned and configured to sense position/s of at least part of the metering device, when the electronic module is attached to the inhaler, to detect at least when the metering device is in the triggered state.

In an aspect, the sensor is non-contact sensor, optionally an optical proximity sensor.

In an aspect, the optical proximity sensor works in the near-infrared spectrum.

In an aspect, the sensor is powered by said at least one battery.

In an aspect, the powder inhaler comprises a casing, optionally a plastic casing, and the electronic module comprises a housing, optionally a plastic housing.

In an aspect, the housing is removably attachable to the casing, optionally by clipping the housing onto the casing or clipping the casing onto the housing.

In an aspect, the container, the inhalation channel and the metering device are housed in the casing.

In an aspect, the casing has a respective window and the housing has a respective window.

In an aspect, when the electronic module is attached to the powder inhaler, the window of the casing faces the window of the housing such that the sensor faces at least part of the metering device.

In an aspect, the sensor is placed in the housing.

In an aspect, the window of the casing and the window of the housing are optically transparent windows. Said windows are transparent in the relevant electromagnetic spectra for the optical proximity sensor.

In an aspect, the electronic control unit is configured to perform execution of a task comprising at least the following steps:
  reading an output signal from the non-contact sensor at regular intervals;
  optionally, filtering the output;
  comparing the output with a threshold value and discerning if the metering device is in the triggered state or not.

In an aspect, the inhaler comprises the casing and a cover rotatably coupled to the casing.

In an aspect, the electronic module is attached or attachable onto a portion of the inhaler opposite with respect to the cover.

In an aspect, the cover is moveable between a closed position, in which it covers the mouthpiece, and an open position, in which it exposes the mouthpiece.

In an aspect, the electronic module comprises a cover open switch configured to detect opening of the cover of the inhaler.

In an aspect, the cover open switch is operatively connected to the electronic control unit.

In an aspect, the cover open switch is mounted on the printed circuit board.

In an aspect, the cover open switch is powered by said at least one battery.

In an aspect, an opening of the cover beyond a range of rotational movement of the cover from the closed position of said cover triggers the cover open switch, which optionally causes activation of the non-contact sensor.

In an aspect, the cover open switch is the main switch or is operatively connected to the main switch such that transition of the electronic module from the rest configuration to the working configuration is triggered through the cover open switch.

In an aspect, the electronic module comprises an attachment detection switch interacting with the inhaler when the electronic module is attached to the inhaler to detect connection or disconnection of the electronic module to/from the inhaler.

In an aspect, the attachment detection switch is operatively connected to the electronic control unit.

In an aspect, the attachment detection switch is mounted on the printed circuit board.

In an aspect, the attachment detection switch is powered by said at least one battery.

In an aspect, attaching the electronic module to the inhaler triggers the attachment detection switch, which optionally causes activation of the cover open switch.

In an aspect, the attachment detection switch is the main switch or is operatively connected to the main switch such that transition of the electronic module from the rest configuration to the working configuration is triggered through the attachment detection switch.

In an aspect, the electronic control unit is configured to store in the storage memory and/or to send to the external electronic device, via the communication interface, data related to events of the inhaler, such as, for instance, triggering of the metering device and/or attachment/detachment of the electronic module to/from the powder inhaler and/or opening/closing of the cover.

In an aspect, the electronic control unit is configured first to store said data in the storage memory and then, after a time delay, to send said data to the external electronic device.

In an aspect, the electronic control unit is configured to send, on demand, said data to the external electronic device. Data can be stored only in the electronic control unit as long as a connection with an external electronic device is not available. Therefore, the electronic control unit does not need an external electronic device to properly work and save data.

DETAILED DESCRIPTION

Figure 1:
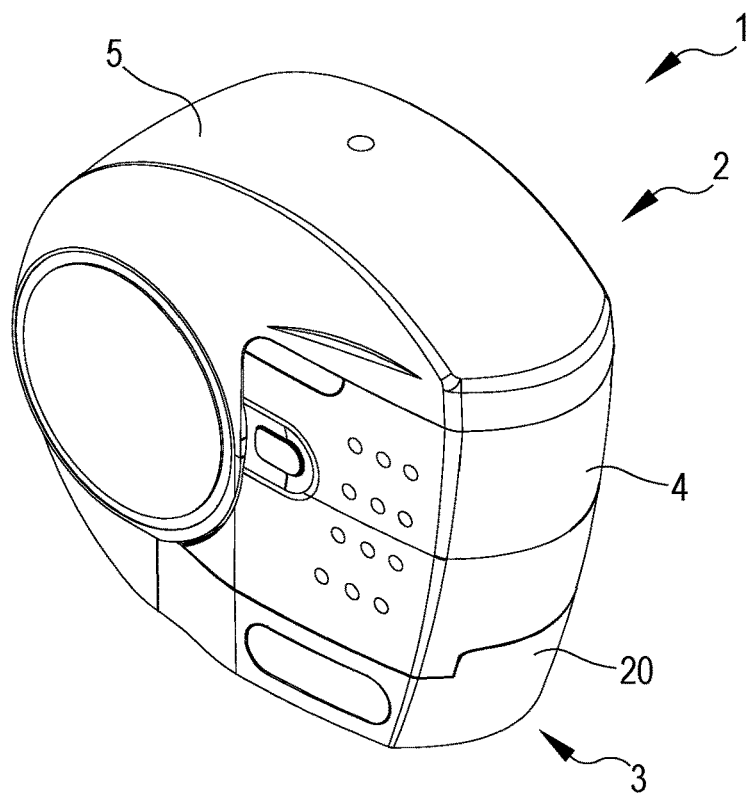
FIG. 1 shows an isometric view of an inhaler assembly comprising an inhaler and an electronic module according to the present invention in a closed configuration.
Figure 2:
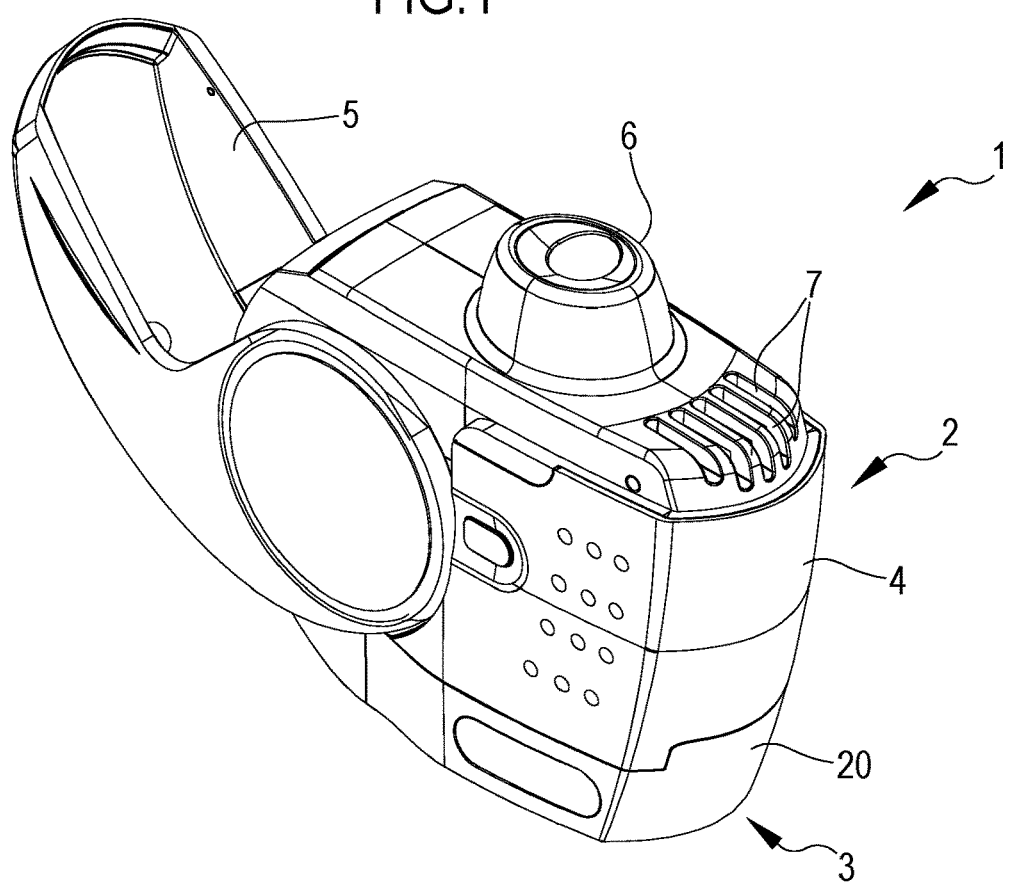
FIG. 2 shows an isometric view of the inhaler assembly of FIG. 1 in an open configuration.

With reference to the appended drawings, FIG. 1 and FIG. 2 show an inhaler assembly 1 according to the present invention. The inhaler assembly 1 comprises a powder inhaler 2 and an electronic module 3. The powder inhaler 2 may be substantially the same as the one disclosed in document WO 2004/012801 or in document WO 2016/000983A1 of the same Applicant. Therefore, only the main parts and the differences with respect to WO 2004/012801 or WO 2016/000983A1 will be detailed in the following description. The electronic module 3 (add-on module) is intended to be supplied separately from the inhaler 2 and to be assembled by the user upon first-time use. For example, the electronics within the electronic module 3 is fully built and assembled up to two years before the first use in the field, thus requiring a minimum shelf-life of twenty-four months prior to its in-use life which is specified as a further twelve months.

Powder Inhaler

The powder inhaler 2 shown in FIG. 1 comprises a plastic casing 4 and a plastic cover 5 being pivotably or rotatably coupled to the casing 4. As shown in FIG. 2, the cover 5 can be opened to reveal a mouthpiece 6 through which a user can inhale a powdered medicament. At an upper front side of the mouthpiece 6, slots 7 are formed in the casing 4 which allow air inlet.

Figure 5:
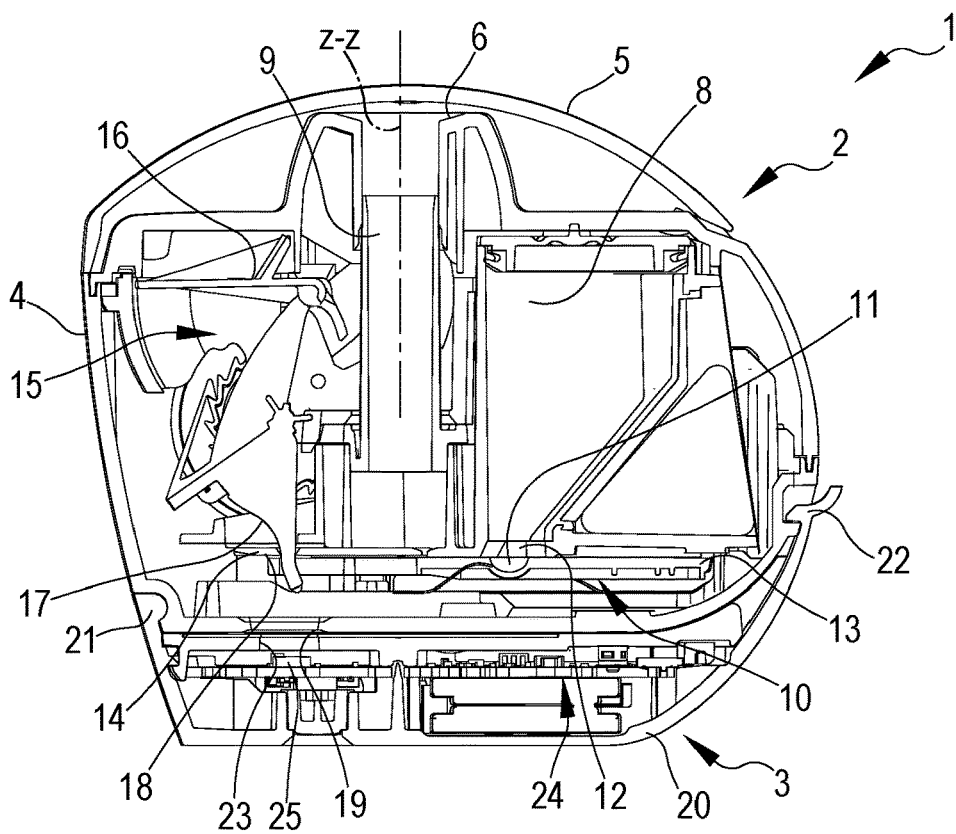
FIG. 5 is a section view of the inhaler assembly of the previous figures with the cover closed.

The powder inhaler 2 comprises a container 8 for storing a powdered medicament, an inhalation channel 9 connected to the mouthpiece 6 and a metering device 10 (FIG. 5). The inhalation channel 9 has a first opening connected to the mouthpiece and a second opening, opposite with respect to the first opening. As shown in FIG. 5, all these elements are housed inside the casing 4.

The container 8 is filled or is configured to be filled with an amount of powder medicament corresponding to a plurality of doses, e.g. up to 100-200 doses. The metering device 10 is a mechanism comprising a plurality of moving components.

The metering device 10 is movable, with respect to the container 8 and with respect to the inhalation channel 9, between an idle state (shown in FIG. 5), in which a dosing recess 11 is in communication with an opening 12 of the container 8 so as to be filled with a dose of the powdered medicament, and a triggered state (not shown in the attached figures), in which the dosing recess 11 is in placed under the inhalation channel and in communication with the inhalation channel 9 for enabling inhalation of the dose of the powdered medicament contained in the dosing recess 11 through the mouthpiece 6.

Figure 6:
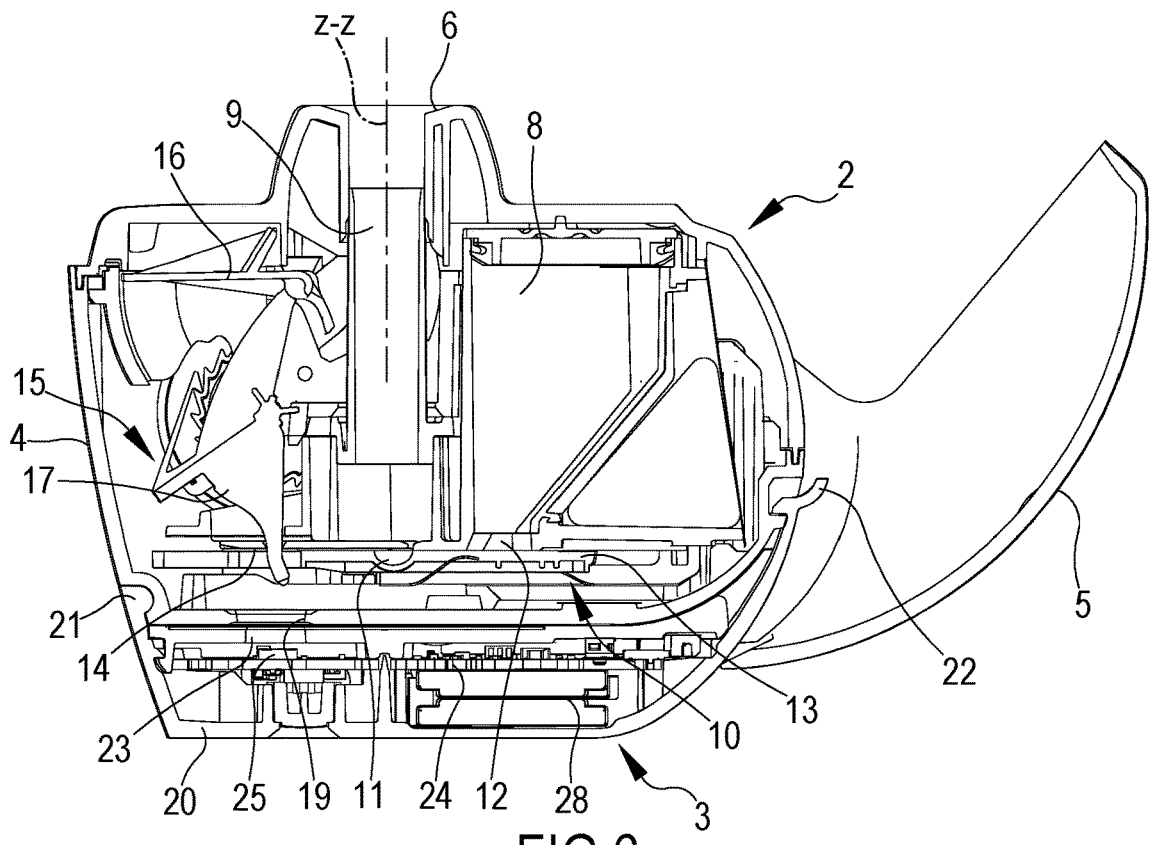
FIG. 6 is a section view of the inhaler assembly of the previous figures with the cover open.

The metering device 10 comprises a shuttle 13 having the dosing recess 11 fashioned on an upper face like a cup shaped recess. The shuttle 13 is slidingly moveable between a filling position (FIG. 5) and an inhalation position (FIG. 6). The filling position corresponds to the idle state (FIG. 5) of the metering device 10, in which the dosing recess is in alignment with the opening 12 of the container 8 so as to be filled with the dose of the powdered medicament. The inhalation position, corresponds to an armed state which, will be detailed later, and to the triggered state of the metering device 10, in which the dosing recess 11 is in alignment with the inhalation channel 9 (FIG. 6).

The shuttle 13 is mechanically coupled to the cover 5 such that an opening of the cover 5 beyond a range of rotational movement from a closed position causes the shuttle 13 to move from the filling position to the inhalation position. Closing of the cover 5 causes the shuttle 13 to move back from the inhalation position to the filling position. FIG. 5 shows the cover 5 in the closed position and the shuttle 13 in the filling position. For instance, the range of rotational movement which causes sliding of the shuttle from the filling position to the inhalation position is eighty degrees.

The metering device 10 further comprises a protective member 14 provided between the shuttle 13 and the inhalation channel 9. The protective member 14 is a transparent or semi-transparent plate arranged between the second opening of the inhalation channel 9 and the shuttle 13. The protective member 14 has a smooth surface finish reflecting light in a specular fashion (mirror-like reflection).

The protective member 14 is parallel with respect to the shuttle 13 and is slidingly movable on the shuttle 13 between a closed position and an open position. In the closed position, the protective member 14 is shifted backwards towards the second opening of the inhalation channel 9 and towards the container 8. In the closed position, a rear part of the protective member 14 may at least in part close the second opening of the inhalation channel 9. In the open position, the protective member 14 is shifted forward towards a wall of the casing 4. In the open position, a rear part of the protective member 14 leaves open the second opening of the inhalation channel 9.

The protective member 14 is in the closed position when the shuttle 13 is in the filling position. The protective member 14 may be moved between the closed position and the open position when the shuttle 13 is in the inhalation position. Therefore, the metering device 10 is configured to take the three different states cited above (idle, armed, triggered) and these states are determined by the positions of the shuttle 13 and of the protective member 14 as disclosed in the following Table 1.

TABLE 1

| State of the metering device | Position of the shuttle | Position of the protective member |
|---|---|---|
| Idle | Filling | Closed |
| Armed | Inhalation | Closed |
| Triggered | Inhalation | Open |

In the idle state, the shuttle 13 is in the filling position and the protective member 14 is in the closed position. The protective member 14 does not cover the dosing recess 11. The dosing recess 11 is communication with the opening 12 of the container 8 to receive the medicament dose (FIG. 5).

In the armed state, the shuttle 13 is in the inhalation position and the protective member 14 is in the closed position. The protective member 14 covers the dosing recess 11. The protective member 14 prevents the powdered medicament contained in the dosing recess 11 from entering into the inhalation channel 9 (FIG. 6).

In the triggered state (not shown), the shuttle 13 is in the inhalation position and the protective member 14 is in the open position. The protective member 14 does not cover the dosing recess 11, thereby exposing the dosing recess 11 to the inhalation channel 9 so as to enable a user to inhale the dose of the powdered medicament contained in the dosing recess 11.

The powder inhaler 2 further comprises an inhalation or breath actuated mechanism 15 coupled to the protective member 14. The inhalation actuated mechanism 15 comprises an inhalation actuated member 16 shaped like a flap, a coupling member 17 and a resilient element, not shown. A further resilient element, not shown in the attached drawings, may be mounted on the coupling member 17 on an opposite side with respect to the resilient element 18 (as in WO 2016/000983). The flap 16 is coupled to the protective member 14 through the coupling member 17 such that, if there is an inhalation suction force exceeding a predetermined value, the flap 16 is moved from a first position to a second position, thereby causing the protective member 14 to move from the closed position to the open position. The flap 16 is placed inside the casing 4 and closes to the slots 7. In the first position (FIG. 5), the flap 16 separates the slots 7 from the inhalation channel 9 and seats in a main airflow path. In the second position, the flap 16 is rotated with respect to the first position to open the slots 7 and to allow air flowing through the slots 7 into the inhalation channel 9 and out of the mouthpiece 6.

The coupling member 17 comprises a prolongation engaging with an opening 18 formed in the protective member 14 in order to move the protective member 14 from the closed position to the open position when the coupling member 17 moves from its respective first position to its respective second position and vice-versa.

The casing 4 has an optically transparent window 19 placed close to the metering device 10 such that the metering device 10 is at least in part visible through the window 19 from outside the casing 4. In particular, the shuttle 13, the protective member 14, and a terminal end of the coupling member 17 are visible through the window 19. While the protective member 14 has a smooth surface finish reflecting light in a specular fashion (mirror-like reflection), the shuttle 13 and the prolongation reflect light more diffusely (scattered reflection). All the elements of the powder inhaler 2 may be made of plastic material.

Electronic Module

The electronic module 3 is configured to be attached in removable manner to the powder inhaler 2 so that the same electronic module 3 may be used with another new powder inhaler 2 once the medicament in the old inhaler is over. In the embodiment shown in the attached Figures, the electronic module 3 is attached or attachable onto a portion of the powder inhaler 2 opposite with respect to the cover 5.

The electronic module 3 comprises a plastic housing 20 removably attachable to the casing 4 of the powder inhaler through a clip-on coupling. The non-limiting embodiment of the housing 20 of the electronic module 3 shown in the attached Figures comprises a rigid clip 21 and a flexible clip 22 shaped to couple with respective recesses of the casing 4 of the powder inhaler 2.

The housing 20 has an upper face configured to face, when the electronic module 3 is attached to the powder inhaler 2, to a lower face of the powder inhaler 2 having the optically transparent window 19. Also, the upper face of the electronic module 3 is provided with a respective optically transparent window 23 and, when the electronic module 3 is attached to the powder inhaler 2, the window 19 of the casing 4 faces the window 23 of the housing 20.

A printed circuit board (PCB) 24 is housed inside the housing 20. The printed circuit board (PCB) 24 carries electronic components. One or more of said electronic components are configured to detect at least a status and/or at least a working parameter of the powder inhaler 2, when the electronic module 3 is attached to the powder inhaler 2.

The electronic components comprise an electronic control unit (i.e. a microprocessor), a wireless communication interface (e.g. Bluetooth), a storage memory electronically connected one to the other. The communication interface is configured to connect the electronic module to an external electronic device, such as a computer, a smartphone, a tablet or the like. All the working parameters and data of the powder inhaler 2 detected through the electronic module 3 may be stored in the storage memory and/or transferred to the external electronic device.

The electronic components further comprise at least one sensor operatively connected to the electronic control unit and configured to detect said at least a status and/or said at least a working parameter of the inhaler.

In the non-limiting embodiment shown in the attached Figures, the electronic components of the electronic module 3 comprise an optical proximity sensor 25 working in the near-infrared spectrum. The optical proximity sensor 25 is placed in the housing 20 and is positioned and configured to sense position/s of at least part of the metering device 10 to detect at least when the metering device 10 is in the triggered state, when the electronic module 3 is attached to the powder inhaler 2. Indeed, when the electronic module 3 is attached to the powder inhaler 2, the window 19 of the casing 4 faces the window 23 of the housing 20 such that the optical proximity sensor 25 faces at least part of the metering device 10, as shown in FIG. 5. The microprocessor may be configured to perform execution of a task comprising at least the following steps: reading an output signal from the optical proximity sensor 25 at regular intervals; filtering the output; comparing the output with a threshold value and discerning if the metering device 10 is in the triggered state or not.

In the non-limiting embodiment shown in the attached Figures, the electronic components of the electronic module 3 further comprises a cover open switch 26 and an attachment detection switch 27. The cover open switch 26 and the attachment detection switch 27 are mounted on the printed circuit board (PCB) 24 and are operatively connected to the microprocessor.

The cover open switch 26 comprises (FIGS. 7, 8, 9, 10 and 11) a mechanical detector switch mounted on the printed circuit board (PCB) 24 and operatively connected to the microprocessor and a spring-loaded mechanical part shaped like an arm 26a. A portion of said arm 26a is placed outside the housing 20 of the electronic module 3 to mechanically interact with the cover 5 of the powder inhaler 2 when the cover 5 is opened beyond a range of rotational movement of said cover 5 from the closed position. An opening of the cover 5 beyond a range of rotational movement of the cover 5 from the closed position of said cover triggers the cover open switch 26, which causes activation of the optical proximity sensor 25.

Figure 3:
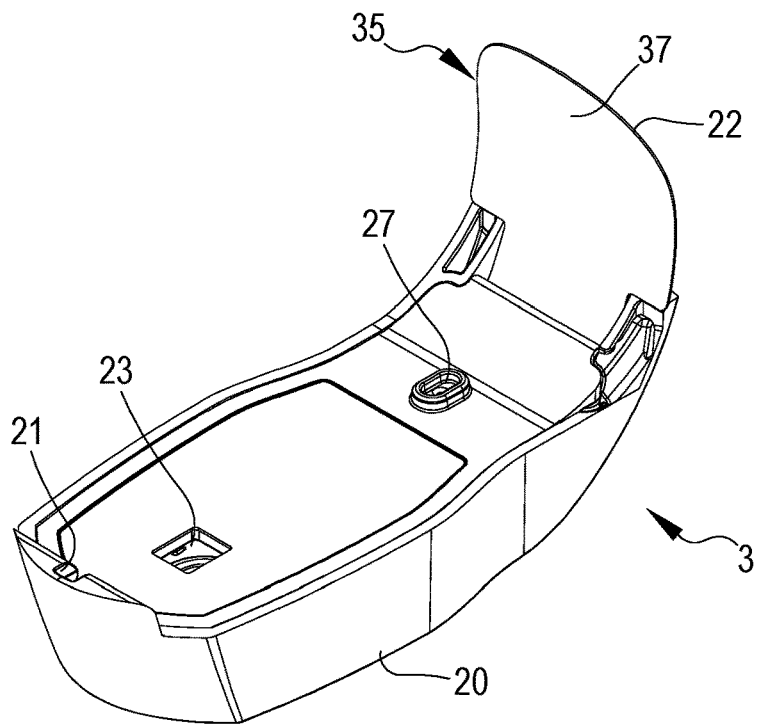
FIG. 3 shows an isometric view of an embodiment of the electronic module of the inhaler assembly of FIGS. 1 and 2, prior to use, with the isolating pull-tab inserted.
Figure 4:
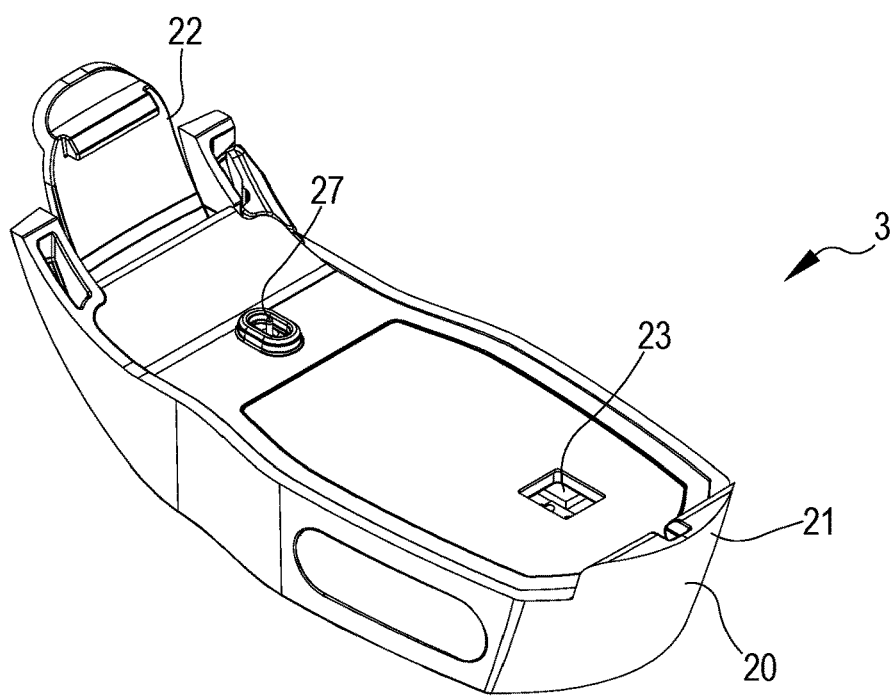
FIG. 4 shows another isometric view of the electronic module of the inhaler assembly of FIGS. 1 and 2.

The attachment detection switch 27 is a mechanical detector switch mounted on the printed circuit board (PCB) 24, operatively connected to the microprocessor and comprising a pin protruding from the upper face of the housing 20 through a respective aperture (FIGS. 3 and 4) to mechanically interact with the powder inhaler 2 when the electronic module 3 is attached to the powder inhaler 2. Attaching the electronic module 3 to the powder inhaler 2 triggers the attachment detection switch 27, which enables the monitoring of the cover open switch 26.

The microprocessor is configured to store in the storage memory and/or to send to the external electronic device, via the communication interface, data related to events of the powder inhaler 2, such as, for instance, triggering of the metering device 10 and/or attachment/detachment of the electronic module 3 to/from the powder inhaler 2 and/or opening/closing of the cover 5.

Figure 7:
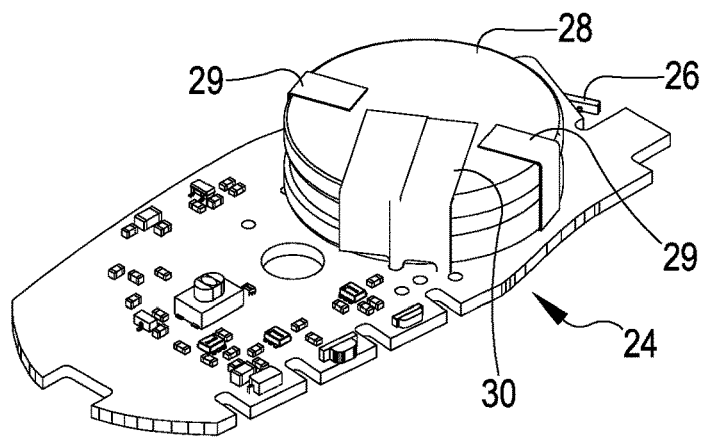
FIG. 7 is an isometric view of a printed circuit board of the electronic module of the previous figures.

The electronic module 3 comprises a pack of non-rechargeable batteries 28 permanently joined to the printed circuit board 24, e.g. two primary coin cells. The batteries 28 of the pack are welded together through metallic tabs 29 and are soldered to the printed circuit board (PCB) 24 by means of through-hole mounted tabs 30 (FIG. 7). Since the batteries 28 are non-rechargeable and non-removable, the electronic module 3 is disposable, i.e., once the batteries 28 are discharged, said electronic module 3 is not reusable and must be discharged.

Figure 12:
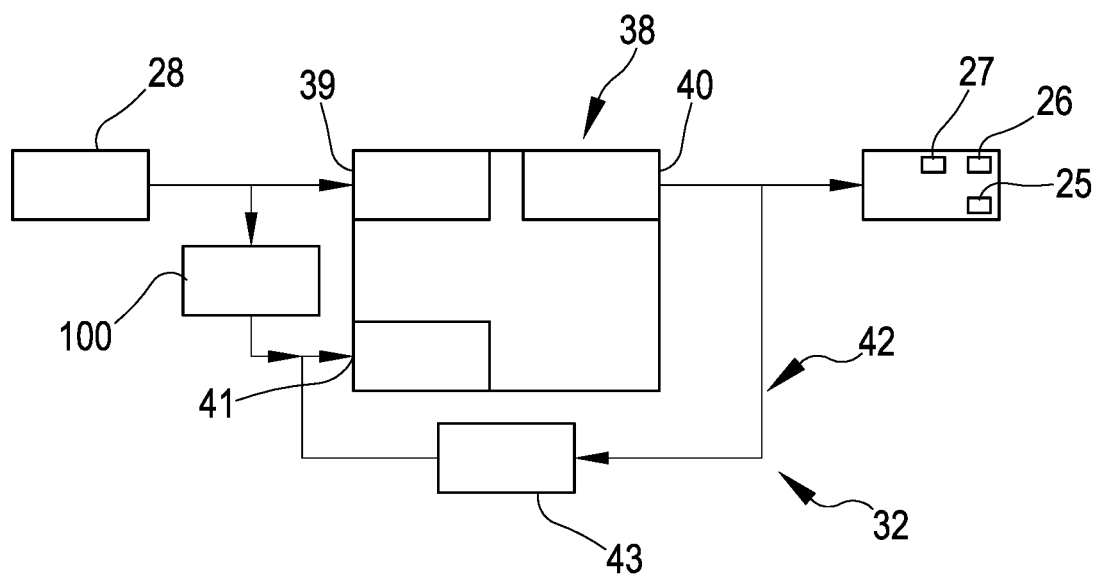
FIG. 12 is a block diagram of part of the printed circuit board of FIGS. 7 to 11.
Figure 13:
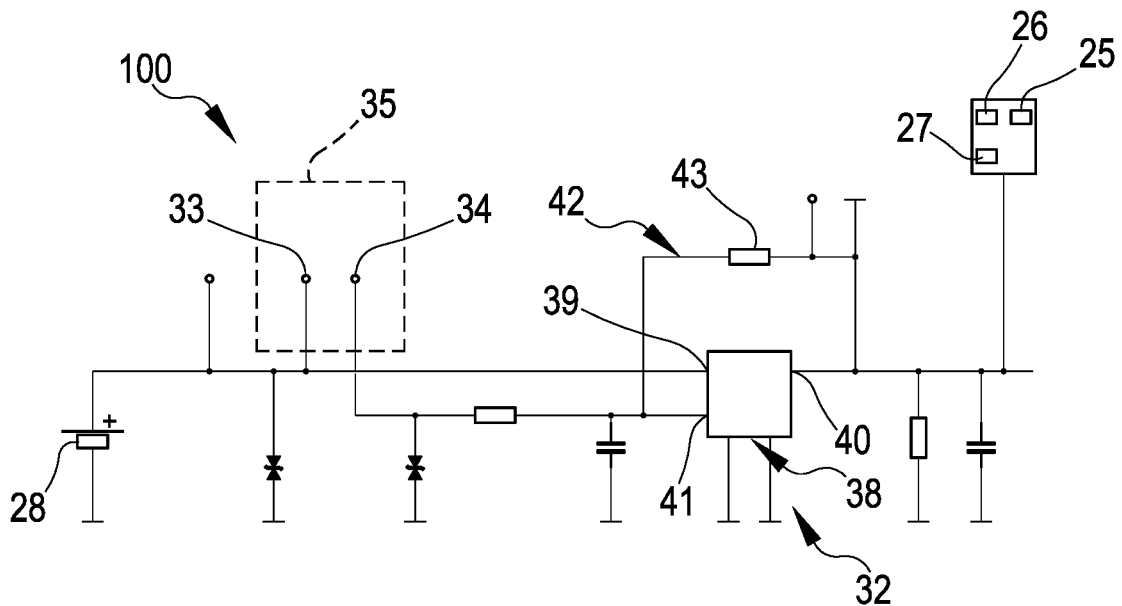
FIG. 13 is an electrical diagram of part of the printed circuit board of FIGS. 7 to 11.
Figure 14:
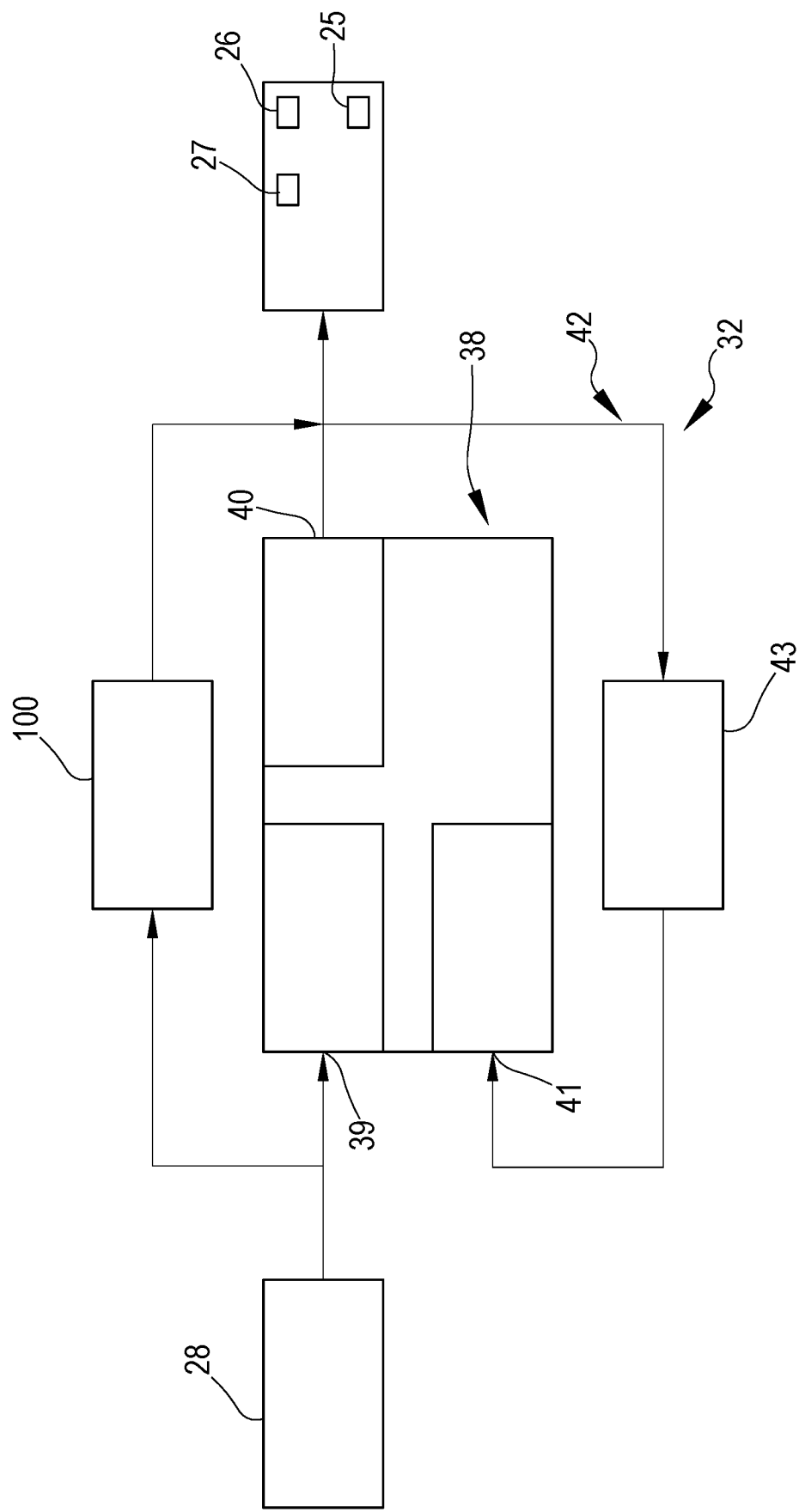
FIG. 14 is a block diagram of a variant embodiment of FIG. 12.

The pack of non-rechargeable batteries 28 is electrically connectable or connected to the electronic components to provide power to said electronic components through a spring loaded contact 31 (FIGS. 8 and 9) and a latching circuit 32 (FIGS. 12, 13 and 14).

The printed circuit board (PCB) 24 comprises (FIG. 9) a first terminal 33 and a second terminal 34 defined by copper pads and electrically connectable one to the other through said spring loaded contact 31 to close a circuit between the batteries 28 and the electronic components and power on the electronic components. The spring loaded contact 31 comprises a metal spring defined by a metal leaf having a first end joined to the printed circuit board (PCB) 24 or to the housing 20 and a second end elastically held against the first terminal 33 and the second terminal 34 (FIGS. 8 and 9).

Figure 8:
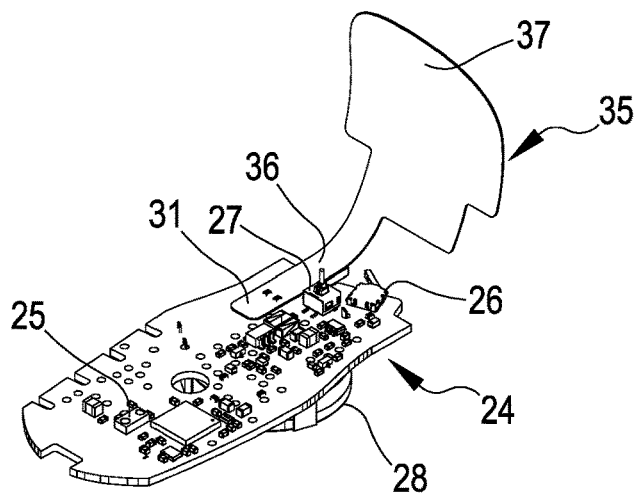
FIG. 8 is another isometric view of an embodiment of the printed circuit board of FIG. 7 with the isolating pull-tab inserted.
Figure 9:
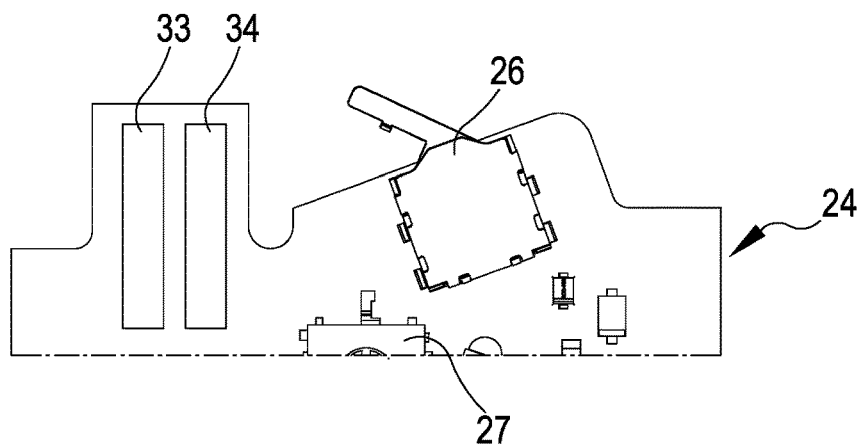
FIG. 9 is an enlarged portion of the printed circuit board of FIGS. 7 and 8.
Figure 10:
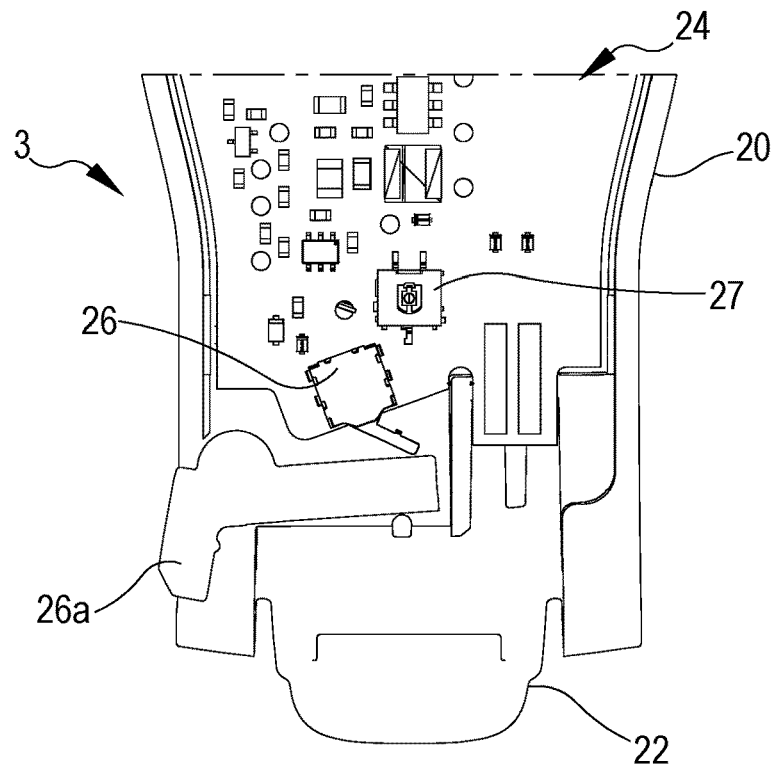
FIG. 10 is portion of the electronic module with some parts removed and in a first configuration.
Figure 11:
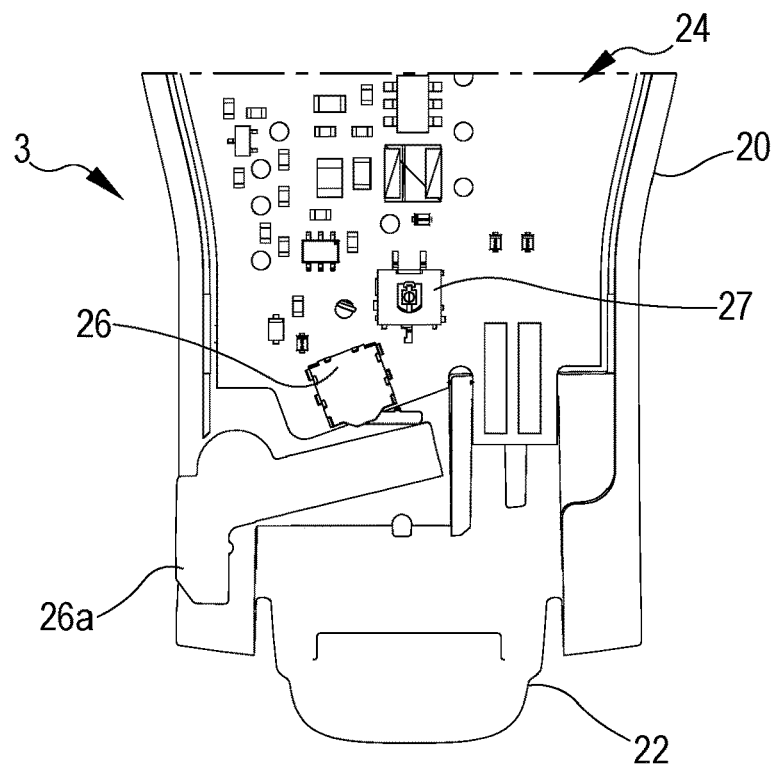
FIG. 11 shows the portion of FIG. 10 in another configuration.

During manufacturing of the electronic module 3, a removable electrical insulating pull-tab 35 is interposed between the metal leaf and the first and second terminals 33, 34 (FIG. 8). Said removable electrical insulating pull-tab 35 remains in place during long-term storage of the electronic module 3 and until the first use by the user. The removable electrical insulating pull-tab 35 is made of a plastic film and comprises an isolating part 36 electrically separating, or configured to electrically separate, the first terminal 33 from the second terminal 34 and a portion 37 having an easy thumb-grip area and configured to be grabbed to allow removing said removable electrical insulating pull-tab 35.

The removable electrical insulating pull-tab 35 is removed by the user before the first use and before attaching the electronic module 3 to the inhaler 2 and is disposed.

In a rest configuration of the electronic module 3 (during long-term storage and before the first use), the isolating part 36 is inserted and interposed between the metal leaf and the first and second terminals 33, 34. The portion 37 protrudes from the housing 20 to allow manually removing said removable electrical insulating pull-tab 35.

In a work configuration of the electronic module 3 (after the first use, when the removable electrical insulating pull-tab 35 has been removed), the metal spring is elastically held against the first terminal 33 and the second terminal 34 and electrically connects the first terminal 33 to the second terminal 34. The metal spring shorts to the contacts on the printed circuit board 24 which then starts the power on of the rest of the circuitry.

Since the cited electrical contact is provided by the elastic force of the metal spring, shocks and/or vibrations may accidentally and momentarily disconnect the first terminal from the second terminal. Therefore, in the disclosed embodiment, the electronic module 3 comprises the latching circuit 32 which is operatively electrically interposed between the batteries 28 and the electronic components.

The latching circuit 32 is configured to maintain powered on the electronic components during accidental and momentary disconnections of the first terminal 33 from the second terminal 34 due to shocks and/or vibrations.

The latching circuit 32 comprises (FIG. 13) a load switch 38 having an input 39 electrically connected to the first terminal 33 and to the batteries 28, an output 40 electrically connected to the electronic components 25, 26, 27 and an enable input 41 electrically connected to the second terminal 34. A feedback electrical path 42 having a 100 kOhm feedback resistor 43 electrically connects the output 40 of the load switch 38 to the enable input 41 of the load switch 38. The load switch 38 has a quiescent current of less than 1 μA, comparable to a self-discharge rate of the batteries 28.

In the rest configuration of the electronic module 3 (during long-term storage and before the first use), the removable electrical insulating pull-tab 35 keeps the batteries 28 disconnected from the enable input 41 of the load switch 38. The load switch 38 is not enabled (input 39 and output 40 are electrically disconnected) and provides isolation of the electronic components 25, 26, 27 from the batteries 28. The load switch 38 adds minimal additional energy demand to the system.

When the removable electrical insulating pull-tab 35 is removed and the first terminal 33 and the second terminal 34 are electrically connected one to the other and form a circuit between the batteries 28 and the enable input 41 of the load switch (work configuration of the electronic module 3), the load switch 38 is enabled and electrically connects the input 39 to the output 40 to power on the electronic components 25, 26, 27.

In the work configuration of the electronic module, during accidentally and momentary disconnections of the first terminal from the second terminal due to shocks and/or vibrations, when the metal spring is deflected away from printed circuit board 28, a signal in the feedback electrical path 42 is configured to keep the load switch 38 enabled and to keep the electronic components 25, 26, 27 powered on. The ON/OFF signal at the enable input 41 of the load switch 38 remains high, thus preventing the disconnection of the power supply.

In other embodiments of the electronic module 3, the first terminal 33 and the second terminal 34 are electrically separated by a main switch 100 (schematically shown in FIGS. 12 and 14) different from the spring loaded contact 31 and the removable electrical insulating pull-tab 35. The main switch 100 is used to remove the electronic device 3 from storage mode. The latching circuit 32 is configured to maintain power supply to the electronic components 25, 26, 27 during momentary disconnections of the first terminal 33 from the second terminal 34 due to a fault of the main switch 100. When the main switch 100 is on, the first terminal 33 and the second terminal 34 are electrically connected one to the other, the load switch 32 is enabled and electrically connects the input 39 to the output 40 to power the electronic components 25, 26, 27. During momentary disconnections of the first terminal 33 from the second terminal 34 due to a fault of the main switch 100, a signal in the feedback electrical path 42 is configured to keep the load switch 100 enabled and to keep the electronic components 25, 26, 27 powered on. The main switch 100 may be a magnetic switch or an optical switch or a relay or an opto-coupler or a touch switch.

In the embodiment of FIG. 13, the feedback is implemented as a resistor 43. Depending on the topology of the load switch 38, other passive components, such as a diode, could be used. Also, active processing methods could be used, such as a general-purpose microcontroller or hardware processing circuitry.

According to FIG. 12, the main switch 100 connects the battery 28 to the enable input 41 of the load switch 38, like in FIG. 13. System current flows through load switch 38, once enabled, and substantially never through the main switch 100 itself.

According to FIG. 14, the main switch 100 is used as a parallel path for system current flow. In this case, system current flows both through the main switch 100 and the load switch 38, once enabled.

In some other embodiments, the cover open switch 26 or the attachment detection switch 27 may be configured to remove the electronic device 3 from storage mode. The cover open switch 26 or the attachment detection switch 27 is the main switch 100 or is operatively connected to the main switch 100, such that the transition of the electronic module 3 from the rest configuration to the working configuration is triggered through the cover open switch 26 or the attachment detection switch 27.

In some other embodiments, the electronic module 3 comprises a button switch, not shown in the attached figures, operatively connected to the wireless communication interface to start pairing the electronic module 3 to the external electronic device. This button switch is the main switch 100 or is operatively connected to the main switch 100 such that transition of the electronic module 3 from the rest configuration to the working configuration is triggered through said button switch.

If the cover open switch 26 or the attachment detection switch 27 or the button switch works as a main switch and is configured to enable the load switch 38, an interface circuitry may be present and is electrically connected to the latching circuit 32 and to said cover open switch 26 or attachment detection switch 27 or button switch.

The invention claimed is:
1. An electronic module for an inhaler, wherein the electronic module is attached or attachable to the inhaler, comprising:
   a printed circuit board comprising electronic components, wherein the electronic components are configured to detect at least a status and/or at least a working parameter of the inhaler when the electronic module is attached to the inhaler;
   at least one battery permanently joined to the printed circuit board;
   wherein the printed circuit board comprises a first terminal and a second terminal electrically connectable one to the other through a main switch to close a circuit between the battery and the electronic components to power on the electronic components;
   wherein, in a rest configuration of the electronic module, the first terminal and the second terminal are electrically separated by the main switch;
   wherein, in a work configuration of the electronic module, the first terminal and the second terminal are electrically connected one to the other through said main switch;
   a latching circuit operatively electrically interposed between the battery and the electronic components, wherein, when the electronic module is in the work configuration, the latching circuit is configured to maintain power supply to the electronic components during momentary disconnections of the first terminal from the second terminal due to a fault of the main switch.

2. The electronic module according to claim 1, wherein the latching circuit comprises:
   a load switch having an input, an output and an enable input, wherein the first terminal is electrically connected to the battery and to the input, the second terminal is electrically connected to the enable input, the electronic components are electrically connected to the output;
   a feedback electrical path electrically connecting the output of the load switch to the enable input of the load switch;
   wherein, when the main switch is on and the first terminal and the second terminal are electrically connected one to the other, the load switch is enabled and electrically connects the input to the output to power on the electronic components;
   wherein, during momentary disconnections of the first terminal from the second terminal, a signal in the feedback electrical path is configured to keep enabled the load switch and to keep the electronic components powered on.

3. The electronic module according to claim 2, wherein the feedback electrical path comprises a passive component or an active component.

4. The electronic module according to claim 3, wherein the passive component is a feedback resistor or a diode, wherein the active component is a microcontroller or a processing circuitry.

5. The electronic module according to claim 1, comprising a removable electrical insulating pull-tab; wherein the main switch comprises at least one spring loaded contact; wherein, in the rest configuration of the electronic module, the first terminal and the second terminal are electrically separated by the removable electrical insulating pull-tab; wherein, in the work configuration of the electronic module, the removable electrical insulating pull-tab is removed and the first terminal and the second terminal are electrically connected one to the other through said at least one spring loaded contact; the latching circuit being configured to maintain power supply to the electronic components during momentary disconnections of the first terminal from the second terminal due to shocks and/or vibrations causing the temporary loss of the spring loaded contact.

6. The electronic module according to claim 5, wherein the removable electrical insulating pull-tab is made of plastic.

7. The electronic module according to claim 5, wherein the electronic module comprises a housing, wherein the printed circuit board assembly is placed inside the housing, wherein the removable electrical insulating pull-tab has a portion protruding from the housing to allow manually removing said removable electrical insulating pull-tab.

8. The electronic module according to claim 5, wherein said at least one spring loaded contact comprises a metal spring; wherein, in the rest configuration of the electronic module, the removable electrical insulating pull-tab is interposed between the metal spring and the first terminal and second terminal; wherein, in the work configuration of the electronic module, the metal spring is elastically held against the first terminal and the second terminal and electrically connects the first terminal to the second terminal.

9. The electronic module according to claim 1, comprising a wireless communication interface configured to connect the electronic module to an external electronic device, and a button switch operatively connected to the wireless communication interface to start pairing the electronic module to the external electronic device; wherein the button switch is the main switch or is operatively connected to the main switch such that transition of the electronic module from the rest configuration to the working configuration is configured to be triggered through the button switch.

10. The electronic module according to claim 1, comprising a cover open switch configured to detect opening of a cover of the inhaler, wherein an opening of the cover of the inhaler is configured to trigger the cover open switch, wherein the cover open switch is the main switch or is operatively connected to the main switch such that transition of the electronic module from the rest configuration to the working configuration is configured to be triggered through the cover open switch.

11. The electronic module according to claim 1, comprising an attachment detection switch configured to interact with the inhaler when the electronic module is attached to the inhaler to detect connection or disconnection of the electronic module to/from the inhaler; wherein the attachment detection switch is the main switch or is operatively connected to the main switch such that transition of the electronic module from the rest configuration to the working configuration is configured to be triggered through the attachment detection switch.

12. The electronic module according to claim 1, wherein the load switch has a quiescent current comparable to a self-discharge rate of said at least one battery.

13. The electronic module according to claim 12, wherein the quiescent current is less than 2 µA.

14. The electronic module according to claim 1, wherein the at least one battery is soldered to the printed circuit board.

15. The electronic module according to claim 1, wherein the at least one battery is non-rechargeable.

16. The electronic module according to claim 1, wherein the electronic components comprise: an electronic control unit and at least one sensor operatively connected to the electronic control unit and configured to detect said at least a status and/or said at least a working parameter of the inhaler.

17. An inhaler assembly comprising:
an inhaler;
the electronic module according to claim 1;
wherein the electronic module is attached or is configured to be attached in a removable manner to the inhaler.

18. The inhaler assembly according to claim 17, wherein the inhaler comprises:
a container for storing a powdered medicament;
a mouthpiece and an inhalation channel connected to the mouthpiece;
a metering device having a dosing recess; wherein the metering device is movable, with respect to the container and the inhalation channel, between an idle state, in which the dosing recess is in communication with an opening of the container so as to be filled with a dose of the powdered medicament, and a triggered state, in which the dosing recess is in communication with the inhalation channel for enabling inhalation of the dose of the powdered medicament contained in the dosing recess through the mouthpiece;
wherein the electronic components of the electronic module comprise: a sensor positioned and configured to sense position/s of at least part of the metering device, when the electronic module is attached to the inhaler, to detect at least when the metering device is in the triggered state.

19. The inhaler assembly according to claim 18, wherein the sensor is an optical proximity sensor; wherein the inhaler comprises a casing and the electronic module comprises a housing; wherein the container, the inhalation channel and the metering device are housed in the casing; wherein the casing has a respective window and the housing has a respective window; wherein, when the electronic module is attached to the powder inhaler, the window of the casing faces the window of the housing such that the sensor faces at least part of the metering device.

20. The inhaler assembly according to claim 17, wherein the inhaler is a powder inhaler.

* * * * *